United States Patent [19]

Berry et al.

[11] Patent Number: 5,384,246

[45] Date of Patent: Jan. 24, 1995

[54] DETERMINATION OF IONS IN FLUIDS BY A PROCESS INVOLVING DISPLACEMENT OF INDICATOR IONS

[75] Inventors: Michael N. Berry, Eden Hills, Australia; Michael-Harold Town, Oberhausen, Germany; Georg-Burkhard Kresse, Penzberg, Germany; Uwe Herrmann, Bernried, Germany

[73] Assignees: Boehringer Mannheim GmbH, Mannheim, Germany; The Flinders University of South Australia, South Australia, Australia

[21] Appl. No.: 907,732

[22] Filed: Jun. 22, 1992

Related U.S. Application Data

[60] Division of Ser. No. 696,326, Apr. 30, 1991, abandoned, which is a continuation of Ser. No. 302,799, Jan. 19, 1989, abandoned.

Foreign Application Priority Data

Apr. 10, 1987 [AU]  Australia ........................ PI1365
Jun. 5, 1987 [AU]  Australia ........................ PI2311

[51] Int. Cl.$^6$ .......... C12Q 1/40; C12Q 1/00; C12Q 1/34; C12Q 1/26
[52] U.S. Cl. .......................... 435/22; 435/7.7; 435/7.72; 435/18; 435/25; 435/962
[58] Field of Search .............. 435/4, 7.7, 7.72, 18, 435/22, 25, 962

[56] References Cited

U.S. PATENT DOCUMENTS

| | | | |
|---|---|---|---|
| 4,657,854 | 4/1987 | Wegfahrt | 435/14 |
| 4,734,375 | 3/1988 | Charlton | 436/74 |
| 4,812,400 | 3/1989 | Steinman | 435/21 |

FOREIGN PATENT DOCUMENTS 0275398  7/1988  European Pat. Off. .

OTHER PUBLICATIONS

Outlaw W. H., Measurement of $10^{-7}$–$10^{-12}$ mol of Potassium . . . Anal Biochem 92, 370–374 1979.
Wimmer M. C., A Kinetic Colorimetric Procedure for Quantifying Mg in Serum, Clin Chem 32/4 629–632 1986.

*Primary Examiner*—Michael G. Wityshyn
*Assistant Examiner*—Ralph Gitomer
*Attorney, Agent, or Firm*—Felfe & Lynch

[57] ABSTRACT

A process and a reagent for the determination of ions in fluids, wherein the influence of these ions on the activity of an enzyme is measured. The ions for example are sodium, potassium, calcium, magnesium, manganese, lithium, lead, zinc, copper, iron or other heavy metals or non-metallic ions comprising chloride, bicarbonate, protons, ammonium and substances that give rise to ammonium. The enzymes which are used may be a transferase, a hydrolase, an oxidoreductase or a lyase. An essential feature is a method to exclude interferences by ions by masking the interfering ions with a binding agent.

23 Claims, No Drawings

DETERMINATION OF IONS IN FLUIDS BY A PROCESS INVOLVING DISPLACEMENT OF INDICATOR IONS

This is a division of application Ser. No. 07/696,326 filed on Apr. 30, 1991, which is a continuation of application Ser. No. 07/302,799 filed on Jan. 19, 1989, now abandoned, based on PCT/EP88/00275 filed on Apr. 2, 1988.

This invention is concerned with methods and reagents for the determination of ions, hereinafter also called analytes, in biological and non-biological fluids.

The invention is based on the ability of many analytes to stimulate or inhibit the activity of a sensitive enzyme. The analytes may be cations or anions, metallic or non-metallic, simple or compound. In practice it is frequently found that the analyte is present in the sample at a concentration that lies outside the range of sensitivity of the relevant analytical indicator enzyme, or that interference is caused by the presence of other ions to which the enzyme is also sensitive. This invention addresses and solves these problems in diverse ways.

In the practice of Clinical Biochemistry the measurement of serum electrolytes are the most common analytical tests performed within hospitals. These measurements are requested not only for routine investigations but frequently for emergency and life-threatening situations where speed of analysis is essential. Since a major source of delay in hospitals is the transport of specimens from the wards to the diagnostic laboratories, a method that is easily performed near the bed-side would be of particular value in emergency situations.

A common method of analysing potassium and sodium in clinical biochemistry practice is flame photometry. This process depends on the principle that certain atoms when energized by heat become excited and emit light of a characteristic wavelength when returning to ground state. The intensity of the characteristic wavelength of radiant energy produced by the atoms in the flame is directly proportional to the number of atoms excited in the flame, which is directly proportional to the concentration of the substance of interest in the sample. The apparatus required is complex and relatively expensive and requires the use of combustible gases.

An alternative method especially for sodium, potassium and chloride makes use of ion-selective electrodes. Ideally, each electrode would possess a unique ion-selective property that would allow it to respond to only one ion. In practice this is not the case and interfering ions exist for all ion-selective electrodes. Moreover, ion-specific electrodes are not absolutely specific although generally corrections are possible. The electrodes measure the potential developed in the presence of the specific ion. The instrumention is relatively expensive. Neither method can be performed spectrophotometrically and the clinical need for ion measurement therefore results in a substantial increase in the complexity of commercially available clinical analysers, most of which are designed primarily for spectrophotometric assays. Both methods require a considerable degree of skill and knowledge for their successful implementation.

Similarly, the routine determination of chloride by coulometric methods requires special instrumentation. The endpoint of this titration procedure is detected by an increase in electrical flux completion of formation of insoluble silver chloride product. Alternatively, potentiometric determinations may be used which are also very time consuming and involve additional instrumentation.

For chloride, in addition, there are a number of photometric and titrimetric methods, which e.g. include:
   titrimetric determination of free $Hg^{2+}$ ions via diphenylcarbazone complex
   colorimetric determination of the rhodanide complex of iron, which is formed after dissociation of the mercury complexes upon precipitation of $HgCl_2$ (Skeggs, Clin. Chem. 10, 1964, 918f.; Schmidt, Zentralblatt Pharm. 124 (9), 1985, 527f)
   colorimetric determination of chloranilic acid from the respective mercury salt (Renschler)
   determination of the coloured $Cu^{2+}$ complex of diethyldithiocarbaminic acid from the colourless mercury salt (German Offenlegungsschrift 2137146)
   the rather common TPTZ-method (tripyridile-s-triazine) (R. Fried, Zeitschr. Klin. Chem., Klin. Bloch. 10, 1972, 280f; DOS 215 3387) which is similarily based on the formation of a coloured metal complex upon dissociation of a mercury complex.

A major drawback of these methods is the use of solutions containing highly toxic substances. Some of the methods are complicated and imprecise (e.g. the titration method). Many of the reagents are unstable and calibration curves are non-linear (e.g. the rhodanide method). Some of these methods in addition need a pretreatment in order to eliminate interferences by the protein content of the sample.

An improved TPTZ-method is described in Wo. 83/002670, the use of toxic mercury compounds however is still a disadvantage. The only colorimetric method without use of mercury ions is the determination of hexachlorocomplexes of Fe(III) in a perchloric acid solution (F. Hoppe., Ther. Ggw. 110(4), 1971, 554f.; H. Mahner, Zeitschr. Klin. Chem., klin. Biochem. 11(11), 1973, 451f.; W. T. Law, Clin. Chem. 26 (13) 1980, 1874f.; U.S. Pat. No. 4278440). A considerable limitation of this method is the use of strongly acid reagents which are corrosive and therefore not compatible with mechanical pipetting systems. A further disadvantage is the interference by bilirubin in the samples.

Calcium is a further example of an electrolyte which is routinely determined in the clinical laboratory. The concentration of this metal ion in body fluids is regulated within a narrow range. Pathologically high or low concentrations can lead to life threatening disorders such as renal insufficiency, pancreatitis, tetany and congestive heart failure.

One of the earliest methods for the determination of calcium was that described by Tisdall (J. Biol. Chem. 63, 461–465, 1925) in which calcium is precipitated by oxalic acid which is in turn estimated colorimetrically. The method involves a centrifugation step and is therefore very time consuming; it is not specific for calcium and depends on a careful handling of samples. The method has been succeeded in many laboratories by titrimetric and direct colorimetric procedures. The former also has the drawback of a complicated and cumbersome procedure and requires large sample volumes. In the latter procedure calcium affects the colour of a dye, for example orthocresolphthalein complexone, which can be measured in a photometer. Due to the simplicity of the method it lends itself to automation in the clinical laboratory. The method, however, involves the use of aggressive, highly alkaline solutions and toxic substances. It is particularly prone to interference by a number of serum components such as lipids, proteins, phosphate and bilirubin and as a result does not agree well with atomic absorption and flame photometric reference methods. A further disadvantage of the colorimetric procedure is that the calibration curves are non-linear and the colour is greatly dependent on temperature.

In W. H. Outlaw and O. H. Lowry, Analytical Biochemistry 92,370–374 (1979) an enzyme-mediated assay for measuring potassium ions in tissues is described. The method employs pyruvate kinase, from rabbit muscle, which is activated by potassium ions and sodium ions, the former being about one forty-fold more effective. Because of this non-specificity the method may be suitable for plant material in which potassium ions are the predominant cations, but it is unsuitable for measurements in body liquids like serum which contains a thirty-fold excess of sodium ions. Therefore sodium ions cause unacceptable interference when using the enzymatic photometric technique as described by Lowry et al. to measure potassium in plasma or serum. A further problem is that ammonium ions give a similar activation to potassium ions. The above mentioned publication does not address or solve these critical problems in regard to the analysis of potassium ions in biological fluids such as serum, nor does it propose any method for the determination of sodium ions.

Therefore, it is an object of the present invention to provide a process and a reagent by which the above mentioned problems are avoided. The invention solves the problems by a process for the determination of ions (analytes) in fluids wherein the influence of these ions on the activity of an enzyme is measured.

A key feature of this invention is the use of selective binding agents to bring the free concentration of the analyte within the optimal range for the analytical enzyme, particularly when dilution of the fluid is not practicable. An additional element of the invention is the use of competitive inhibitors of the relevant analytical enzyme in order to reduce its sensitivity to the analyte, thereby permitting measurement of the latter at a higher concentration. This is especially useful, for example, where selective binding agents are not readily available or are unacceptably expensive.

Another feature of the invention is that selective binding agents are employed to reduce the free concentrations of interfering ions to levels where interference is no longer significant. Use is also made of the fact that a competitive inhibitor may compete more effectively with interfering ions than with the analyte, thereby increasing the sensitivity of the enzyme to the analyte with respect to the interfering ion.

An important element is the choice of optimal reaction conditions, including the selection of an appropriate isoenzyme, such that the stimulatory or inhibitory effects of the analyte are substantially greater that those of the interfering ions. In addition, the action of the analyte and interfering ions on the activity of the analytical enzyme should be additive so that if the concentration of interfering ions is known, the concentration of the analyte can readily be determined by difference. Where an interfering ion is known to occur at a relatively constant concentration in the fluid under analysis, allowance can be made for this by including an appropriate concentration of the interfering ion in standard (calibrating) solutions. Another method for assaying such analytes is the use of a competitive binding assay where the analyte displaces another ion from a binding agent and the effects of the released ion on the activity of an appropriate enzyme is determined.

These general principles can best be illustrated in detail by showing their application to the determination of potassium, sodium, calcium, chloride and bicarbonate ions in plasma or serum. However, they are applicable to a wide spectrum of ions, for example cations such as magnesium, manganese, lithium, lead, zinc, copper, iron or other heavy metals. Examples of non-metallic ions that can be measured are protons or ammonium. Substances such as urea that give rise to ammonium can also be determined.

Suitable Enzymes

Enzymes which may used can be for example (H. J. Evans et al. Ann. Rev. Plant Physiol. 17, 47, 1966):

Transferases like phosphorous-containing group-transferring transferases. Such a transferase may be pyruvate kinase. In place of pyruvate kinase other kinases such as adenylate kinase or hexokinase, sensitive to magnesium ion or manganous ion may be employed. Another transferase is acetate kinase (from *E. coli*). Another example is pyridoxal kinase from brain which is sensitive to zinc ions.

Hydrolases like glycosidases, for example α- or β-D-galactosidase (from *Escherichia coli*), carboxypeptidase A (from bovine pancreas), collagenase (from *Clostridium hystolicum*), amylase (from saliva or pancreas) or phosphoglycollate phosphatase.

Also peptide hydrolases such as the cysteine or thiol dependent proteinases, specific examples of which are Calpain I and II (also called calcium activated neutral protease) described by Sasaki et al. in J. Biol. Chem. 259, 12489–12494, (1984). The latter enzymes can be isolated and purified from a variety of animal tissues such as: rat liver and kidney, human and porcine erythrocytes, bovine brain, and rabbit skeletal muscle according to the method of A. Kitahara et al., described in J. Biochem. 95, 1759–1766 (1984). A further example is dipeptidyl aminopeptidase I (E.C. 3.4.14.1, Cathepsin C), J. Ken Mc Donald, Bloch. Biophys. Res. Communication 24(5), 66,771f. Another source for the enzymes are proteins obtained by gene recombination techniques.

Oxidoreductases like glycerol dehydrogenase (from *Enterobacter aerogenes*), acetaldehydrogenase (from yeast) or tyrosinase (catechol oxidase).

Lyases like aldolase (from yeast) or carbonic anhydrase (from bovine erythrocytes).

Other suitable enzymes are various enzymes from halophilic organisms. Another source for the enzymes are proteins obtained by gene recombination techniques.

Selective Binding Agents: A wide variety of binding agents are available for the binding of analytes or interfering ions. Such binding or masking substances are cryptands, coronands, crown ethers, podands, spherands, hemispherands, calixarens and combinations thereof, natural occurring ionophores, for example antibiotics, cyclic peptides like valinomycin, complexones and chelating agents, for example iminodiacetic acid, EDTA, nitrotriacetic acid and derivatives thereof. Such compounds are described in Kontakte (Merck), 1977, No. 1, p. 11 ff and p. 29 ff; Kontakte (Merck), 1977, No. 2, p. 16 ff; Konakte (Merck), 1977, No. 3, p. 36 ff; Phase Transfer Catalysts, Properties and Applications (Merck-Schuchardt) 1987, Thermodynamic and Kinetic Data for Cation-Macrocycle Interaction; R. M. Izatt et al., Chemical Reviews 85, 271–339 (1985); Data for Biochemical Research, 1986, R. M. C. Dawson et al., Eds., 3rd edit., 399–415 (Clarendon Press) Oxford; F. Vögtle et al., Chem. Macrocycles, Springer Verlag, New York, 1985; G. W. Gokel et al., Eds., Macrocyclic Polyether Synthesis, Springer Verlag, New York, 1982; M. Hiraoka, Ed., Crown Compounds, Elsevier, Amsterdam, Oxford, N.Y., 1982; J. M. Lehn et al., J. Am. Chem. Soc. 97, 6700–6707 (1975 ); G. Schwarzenbach et al., Helv. Chim. Acta 28, 828 (1945); S. F. A. Kettle, Koordinationsverbindungen, Taschentext 3, Verlag Chemie, Weinheim/Bergstr. 1972; A. E. Martell et al., Die Chemie der Metallchelatverbindungen, Verlag Chemie, Weinheim/Bergstr. 1958; M. Becke-Goehring et al., Komplexchemie, Springer Verlag, 1970; F. Kober, Grundlagen der Komplexchemie, Otto Salle Verlag, Frankfurt/Main 1979; G. Schwarzenbach et al., Helv. Chim. Acta 31, 1029 (1948); R. G. Pearson et al., Science 151,172 (1966).

Examples of chelators capable of binding multivalent ions, in particular bivalent cations are ethyleneglycolbis-(2-aminoethyl ether)-N, N, N', N'-tetraacetic acid (referred to as EGTA) and (ethylenedinitrilo) tetraacetic acid (EDTA). While many binding agents exist that can bind multivalent ions, e.g. EDTA and its derivatives, agents which bind monovalent ions are less common. Tetraphenylboron binds potassium ions. However, a group of compounds with wider possibilities are cryptands which are examples of reagents that can selectively bind monovalent cations in aqueous solutions (R. M. Izatt et al., Chem. Reviews 85, 271–339). Special examples for cryptands are the Kryptofix® compounds of Merck-Schuchardt, for example:

4,7,13,16 21-Pentaoxa-1,10-diazabicyclo[8.8.5]-tricosan, Kryptofix®221, page 438, Merck-Schuchardt catalogue, dated 1987/88, no. 810646 (K 221).

4,7,13,16,21,24-Hexaoxa-1,10-diazabicyclo[8.8.8]hexacosan, Kryptofix®222, page 438, Merck-Schuchardt catalogue, dated 1987/1988, no. 810647 (K222).

As masking compounds for the elimination of interfering anions the following classes of substances may potentially be used:

anioncryptandes, heterocyclophanes, catapinands and inorganic metal complexes or insoluble salts. Special examples of anion complexing compounds are described in the literature, e.g. azamono- or azapolycycles, macrocyclic quarternary tetrahedron compounds, macrocyclic bis -metal-complexes, macrocycles with covalently incorporated lewis acid centers, protonated- or alkylated quarternary cryptands or catapinands (F. P. Schmidtchen, Nachrichten Chem. Techn. lab. 36(1), 1988, S. 8f; E. Graf, J. Amer. Chem. Soc. 98 (20), 1976, 6403f; C. H. Park, J. Amer. Chem. Soc. 90 (9), 1968, 2431f) as well as e.g. the hexachloro complex of Fe (III) or silver nitrate.

Function of Binding Agents: These binding agents are used for the following purposes:

1. The selective binding of interfering ions.
2. To reduce the concentration of the analytes to optimal measuring levels, if dilution of the sample is not feasible.
3. An embodiment of the invention is a process, wherein the binding agent is present and forms a complex with "indicator" ions, from which complex the indicator ions are displaced stoichiometrically by the analyte ions, and wherein the influence of the displaced indicator ions on the activity of an enzyme is assayed, thereby giving an indirect measure of the concentration of analyte ions. For example in such a process the enzyme is pyruvate kinase, the indicator ions are potassium, the binding agent is Kryptofix®221 and the ion to be determined is sodium; or the enzyme is a kinase, the indicator ion is $Mg^{2+}$, the binding agent is a chelating agent, e.g. EDTA, and the ion is a metal, or the enzyme is pyridoxal kinase, the indicator ion is $Zn^{2+}$, the binding agent is Kryptofix®221, and the ion is a heavy metal; or the enzyme is α-amylase, the binding agent is Ag or Hg and the ion to be determined is chloride; or the enzyme is collagenase the binding agent is a chelating agent such as EDTA and the ion to be determined is calcium.

Fluids for Analysis: The biological fluids in which the measurement of analytes is made are blood, serum, plasma, sweat, transudates or exudates or urine for example. Other examples of fluids are tap water or extracts of foodstuffs or fruits or fermented liquids such as wine.

Application of General Principles to the Determination of Potassium and Sodium Ions The essential requirements for a satisfactory method for the determination of potassium ions in serum or plasma, on the basis of the sensitivity of pyruvate kinase to potassium ions, is the overcoming of the interference by sodium and ammonium ions. According to the general principles embodied in this invention this can be achieved by one or more of the following procedures:

1. The selective binding of sodium ions with a suitable binding agent, for example Kryptofix®221.
2. The selection of Bacillus stearothermophilus, rather than rabbit muscle, as the source of pyruvate kinase since the bacterial enzyme has a sensitivity for potassium ions in relation to sodium ions twice as great as the muscle enzyme.
3. Inclusion of ions which are competitive inhibitors of the sensitive indicator enzyme in the assay, for example the use of lithium ions to compete with sodium ions and potassium ions.
4. Enzymatic removal of ammonium ions.

Since lithium ions are less effective as a competitor against potassium ions, the net effect is to increase the relative sensitivity of pyruvate kinase towards potassium ions a further. 50% as compared with sodium ions. Moreover, in the presence of lithium ions the effects of potassium and sodium ions on the activity of pyruvate kinase become additive, rather than co-operative. This allows the possibility of measurement of the concentration of either potassium or sodium ions, provided that the concentration of the other ions is known.

By the use of procedure 2 and 3 in the absence of a binding agent it is possible to obtain a relative sensitivity of pyruvate kinase for potassium versus sodium ions in the order of 100:1. This means that even at extremely abnormal sodium ion concentrations of either 110 or 170 mmol/l, the error in measured potassium ion concentration will not exceed 0.3 mmol/l relative to a normal plasma sodium ion concentration of 140 mmol/l (Example A). This is not regarded as sufficiently accurate for many clinical purposes. However, if the true concentration of sodium ions in the plasma is known, accurate measurement of potassium ions down to ±0.05 mmol/l is feasible (Example B). If procedures 1–3 are combined and a binding agent, e.g. Kryptofix ®211 is included, the relative sensitivity of pyruvate kinase for potassium ions with respect to sodium ions can be increased to >7 500:1. Under these circumstances it is not necessary to know the sodium ion concentration to determine the plasma potassium ion concentration down to 0.05 mmol/l (Example C ).

These methods for potassium ion determination demonstrate the applicability of the general principles embodied in the invention in regard to reduction of interferences. On the other hand the measurement of sodium ions in serum or plasma best illustrates the application of these principles in regulating effective analyte concentration. One means of measuring sodium ions as embodied in this invention is to use an enzyme whose activity is sensitive to sodium ions. An example of such an enzyme is $\beta$-galactosidase (Kuby et al., J. Am. Chem. Soc. 75,890; 1953). However, the range of sodium ion concentration to which this enzyme is most sensitive is much lower than can conveniently be obtained in a plasma sample, without a dilution step.

In keeping with the principles embodied in this invention the following procedures are employed to lower the effective sodium ion concentration to optimal levels when dilution of the sample is not feasible.
1. Use of a sodium ion binding agent such as Kryptofix ®221.
2. Use of lithium ions as a competitive inhibitor of $\beta$-galactosidase, thereby decreasing the sensitivity of the enzyme to sodium ions.

The combination of procedures 1 and 2 readily allows the determination of sodium ions in plasma or serum, using $\beta$-galactosidase, and the amount of binding agent can be manipulated to minimise the signal for sodium ion concentrations below 110 mmol/l while enhancing the signal in the usual analytical range (110–170 mmol/l) (Example D).

Sodium ions may also be measured by means of pyruvate kinase, provided that conditions are chosen whereby the stimulation of enzyme activity by potassium ions is reduced, and a potassium ion-binding agent, e.g. Kryptofix ®221, is included in the reaction mixture (Example E).

In another method of determining plasma sodium ion concentration, the sodium ions are allowed to displace potassium ions from Kryptofix ®221, the released potassium ions stimulating the activity of pyruvate kinase in proportion to the plasma sodium ion concentration (Example F).

Other embodiments of the invention are compositions and reagents for the determination of ions in biological and non-biological fluids.

The reagent according to the present invention can be present in dissolved or dry form. It can be present impregnated on an appropriate carrier. A diagnostic agent in the form of a test strip can be produced by impregnating a carrier material, preferably filter paper, cellulose or synthetic fibre fleece, with solutions of the necessary reagents conventionally used for the production of test strip in readily volatile solvents, such as acetone. This can take place in one or more impregnation steps. The finished test papers can be used as such or stuck in known manner on to handles or preferably sealed between synthetic resins and fine meshes.

The embodiments of the invention are described hereunder in some detail but it will be seen that the invention need not necessarily be limited in any one or in a combination of the details described, and in particular, mechanical or chemical variations can be utilized besides those described in this embodiment.

Detailed Description of Analytical Methods for Potassium Ions

This section describes in more detail methods for potassium ion determination embodying the principles described in this invention. For the determination of potassium ions, a fluid, for example blood plasma, is incubated with a buffered mixture containing adenosine diphosphate (ADP), phosphoenolpyruvate (PEP), reduced nicotinamide adenine dinucleotide (NADH), pyruvate kinase (PK) and lactate dehydrogenase (LDH). The formation of pyruvate, and subsequently lactate in this mixture, in reactions catalysed by PK and LDH, is entirely dependent on the presence of appropriate cations, in the absence of which PK is virtually inactive. NADH absorbs strongly at 340 nm, whereas NAD does not.

Under the conditions chosen for analysis which include the presence of manganese ions which are required by the bacterial PK, the rate of NADH oxidation is proportional to the concentration of potassium ions (see Examples A–C).

Under these conditions the following reactions take place:

(1) PEP + ADP + H+ 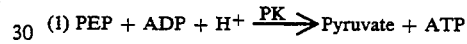 Pyruvate + ATP (2) Pyruvate + NADH + H+ 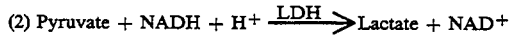 Lactate + NAD+

The rate of reaction (1) is determined by the concentration of potassium ions present in the system, and this in turn limits the rate of reaction (2). There are several ways in which the rates of these reactions can be measured. A standard approach is the spectrophotometric measurement of the rate of disappearance of NADH in reaction (2). NADH absorbs strongly at 340 nm, whereas NAD does not. Accordingly, the fall in absorbance of the reaction mixture at 340 nm (or an alternative wavelength) provides a direct measure of the rate of the reaction and from this the concentration of potassium ions present in the mixture can be derived. Alternatively, advantage can be taken of the fact that both reaction (1) and (2) consume H+, thus lowering the proton concentration of the reaction mixture. The rate of fall in proton concentration can be measured with a pH meter, or by means of a titration procedure. In these latter cases the concentration of buffer employed will be much less than in the spectrophotometric technique. Other equipment such as fluorimeters or luminometers can be used to monitor the activity of pyruvate kinase.

There are a number of other methods of detecting the accumulation of pyruvate associated with PK activity. These include any method for measuring the inorganic phosphate or oxygen consumed or the hydrogen peroxide; acetyl phosphate or carbon dioxide generated by the enzymatic action of pyruvate oxidase; the formation of the hydrazone with 2,4-dinitrophenylhydrazine; the measurement of the reactants or products of the enzymatic action of pyruvate carboxylase; pyruvate decarboxylase or pyruvate dehydrogenase; the use of flavine coupled systems; and isotopic methods for measuring minute concentrations of substrates (M. N. Berry et al., Analytical Biochem. 118,344–352 (1981)).

In a survey of 200 serum samples good agreement has been obtained with other methods such as flame photometric or ion-selective electrode measurements. A significant interference with the method is ammonium ions which are generally present in serum or accumulate on standing. The possibility of ammonium ion interference can be completely avoided by including α-ketoglutarate (KG) and glutamate dehydrogenase (GDH) in the reaction mixture. Ammonium ions are removed in a preincubation according to the reaction:

$NH_4^+ + KG + NADH \rightarrow glutamate + NAD^+$

In solutions such as urine in which the ammonium ion content may be high a coupled reaction can be used.:

$NH_4^+ + KG + NADPH \rightarrow glutamate + NADP$
glucose-6-P + NADP → 6-phosphogluconate + NADPH The coupled method employs glucose-6-phosphate dehydrogenase. Provided that the added glucose-6-P and KG are in excess of any ammonium ions present, all ammonium ions will be removed while preserving the NADH in the reagent.

Typical concentration ranges of the main reagents for the enzymatic determination at 37° C. of potassium ions using a 10 μl sample of plasma or serum are:

PK (*B. stearothermophilus*) 50 U/l to 10 000 U/l
PEP (neutralized Tris salt) 0.3 mmol/l to 30 mmol/l
Kryptofix ®221 0 mmol/l to 30 mmol/l
NADH 0.01 mmol/l to 0.8 mmol/l
buffer, pH 7-8 50 mmol/l to 500 mmol/l
$Mn^{2+}$ or $Mg^{2+}$ 1 mmol/l to 10 mmol/l
LiCl 2 mmol/l to 100 mmol/l
ADP (free acid ) 0.5 mmol/l to 10 mmol/l
LDH (assayed at 25° C.) 5 000 U/l to 100 000 U/l
Serum albumin 0 g/l to 5 g/l
GDH (assayed at 25° C.) 2 500 U/l to 20 000 U/l
KG (free acid ) 1 mmol/l to 10 mmol/l Another example sensitive to potassium ions is glycerol dehydrogenase (E. C. C. Linet al., B 235, 1820, 1960). Typical concentration ranges of the main reagents for the enzymatic determination at 37° of potassium ions using glycerol dehydrogenase are:

Glycerol dehydrogenase 50 U/l to 1000 U/l
Glycerol 0.3 mol/l to 3 mol/l
Kryptofix ®221 0 mmol/l to 30 mmol/l
NAD 0.1 mmol/l to 5.0 mmol/l
buffer, pH 9 20 mmol/l to 500 mmol/l
Serum albumin 0 g/l to 5 g/l
GDH (assayed at 25° C.) 2 500 U/l to 20 000 U/l
KG (free acid ) 1 mmol/l to 10 mmol/l Another enzyme sensitive to potassium ions is acetaldehyde dehydrogenase (S. Black, Arch. Blochem. Biophys. 34, 86, 1951). Typical concentration ranges of the main reagents for the enzymatic determination at 37° C. of potassium ions using acetaldehyde dehydrogenase are:

Acetaldehyde dehydrogenase 50 U/l to 10 000 U/l
Glycolaldehyde 0.3 mmol/l to 30 mmol/l
Kryptofix ®221 0 mmol/l to 30 mmol/l
NAD 0.05 mmol/l to 2.0 mmol/l
buffer, pH 7-8 50 mmol/l to 500 mmol/l
Dithiothreitol 0.1 mmol/l to 2 mmol/l
Serum albumin 0 g/l to 5 g/l
GDH (assayed at 25° C) 2 500 U/l to 20 000 U/l
KG (free acid) 1 mmol/l 10 mmol/l Acetaldehyde (0.02 mmol/l to 1 mmol/l) may be substituted for glycolaldehyde.

Acetaldenyde dehydrogenase also exhibits esterase activity so that potassium ion concentration can be determined by monitoring the release of 4-nitrophenol from 4-nitrophenyl acetate. Typical concentration ranges of the main reagents for the enzymatic determination at 37° C. of potassium ions based on the esterase activity of acetaldehyde dehydrogenase are:

Acetaldehyde dehydrogenase 50 U/l to 10 000 U/l
4-nitrophenyl acetate 0.1 mmol/l to 2 mmol/l
Kryptofix ®221 0 mmol/l to 30 mmol/l
NADH 0,001 mmol/l to 0.1 mmol/l
buffer, pH 7-8 50 mmol/l to 500 mmol/l
Dithiothreitol 0.1 mmol/l to 2.0 mmol/l
Serum albumin 0 g/l to 5 g/l
GDH (assayed at 25° C.) 2 500 U/l to 20 000 U/l
KG (free acid ) 1 mmol/l to 10 mmol/l Determination of Sodium Ions In principle the measurement of sodium ions, using PK, is similar to that of potassium ions, however, certain key differences exist. In the first instance PK is some 40-100 times more sensitive to potassium ion than it is to sodium ion, depending on incubation conditions as described above. Hence even though sodium ions occur in the plasma at a concentration some 30 times that of potassium ions, the latter can interfere with sodium ion measurement.

According to the general principles espoused in this invention, lithium ions are omitted, PK from rabbit muscle is preferred to the bacterial enzyme, and magnesium ions may be substituted for manganese. Inane method the potassium ions are specifically bound with Kryptofix ®222 and the effects of sodium ions on PK activity measured directly (Example E).

Typical concentration ranges of the main reagents for the enzymatic determination at 37° C. of sodium ions using pyruvate kinase are:

PK (rabbit muscle) 50 U/l to 10 000 U/l
PEP (neutralized Tris salt) 0.3 mmol/l to 30 mmol/l
Kryptofix ®222 0.4 mmol/l to 4 mmol/l
NADH 0.01 mmol/l to 0.8 mmol/l
buffer, pH 7-9 50 mmol/l to 500 mmol/l
$Mg^{2+}$ 1 mmol/l to 10 mmol/l
ADP (free acid ) 0.5 mmol/l to 10 mmol/l
LDH (assayed at 25° C.) 5 000 mmol/l to 100 000 U/l
Serum albumin 0 g/l to 5 g/l
GDH (assayed at 25° C. ) 2 500 U/l to 20 000 U/l
KG (free acid ) 1 mmol/l to 10 mmol/l In another method the sodium ions are allowed to displace potassium ions from Kryptofix ®221, the released potassium ions stimulating the activity of PK to a degree dependent on the sodium ion concentration (Example F).

Typical concentration ranges of the main reagents for the enzymatic determination at 37° C. of sodium ions using pyruvate kinase to measure the displacement of potassium ions from Kryptofix ®221 are:

PK (rabbit muscle) 50 U/l to 10 000 U/l
PEP (neutralized Tris salt) 0.3 mmol/l to 30 mmol/l
Kryptofix ®221 1 mmol/l to 10 mmol/l NADH 0.01 mmol/l to 0.8 mmol/l
buffer, pH 9–10 50 mmol/l to 500 mmol/l
$Mg^{2+}$ 1 mmol/l to 10 mmol/l
ADP (free acid) 0.5 mmol/l to 10 mmol/l
LDH (assayed at 25° C.) 5 000 mmol/l to 100 000 U/l
KCl 2 mmol/l to 10 mmol/l
Serum albumin 0 g/l to 5 g/l
GDH (assayed at 25° C.) 2 500 U/l to 20 000 U/l
KG (free acid) 1 mmol/l to 10 mmol/l A more accurate and precise embodiment for determining uses a sodium ion dependent enzyme such as g-galactosidase. (Example D).

Blood plasma is incubated with a buffered mixture containing 2-nitrophenyl-β-D-galactopyranoside (NPG) and the enzyme β-D-galactosidase. The reaction catalysed by β-D-galactosidase is dependent on the presence of sodium ions and the rate of activity is a measure of sodium ion concentration. A key feature of this method is the use of an appropriate amount of sodium ion-selective binding agent (e.g. Kryptofix ®221) for measurements in serum or other biological fluids where the sodium ion concentration may exceed 100 mmol/l, to reduce sodium ion concentration so that the enzyme is most sensitive to small changes in sodium ion concentration in the usual analytical range (110–170 mmol/l). Under the conditions chosen for analysis, which include the presence of moderately high concentrations of magnesium and lithium ions, the rate of 2-nitrophenol and galactose formation is virtually proportional to the concentration of sodium ions being measured. Magnesium ions are required for optimal β-galactosidase activity. Lithium ions are competitive with sodium ions and therefore raise the $K_m$ of the enzyme for sodium ions.

As substrate for β-D-galactosidase many other compounds are suitable. Quite generally, the galactosidase-containing sample is mixed with an appropriate β-D-galactosidase substrate, the substrate being split by the enzyme, one of the fission products then being detected in an appropriate manner. Either the glycone liberated by action of the enzyme or the aglycone can be measured. As a rule, the latter is determined. As substrate, the natural substrate lactose can be used, but especially advantageous is use of a chromogenic galactoside. Thus, in Biochem. Z., 333,209 (1960), there are described phenyl-β-D-galactoside, as well as some further derivatives substituted on the aromatic ring, for example, 2-nitrophenyl-β-D-galactoside (NPG) and 3-nitrophenyl-β-D-galactoside, as substrates of β-D-galactosidase. The phenols liberated by hydrolysis are determined photometrically in the UV range or, in the case of the nitrophenols, in the short-wave visible wavelength range. An oxidative coupling with aminoantipyrine can also follow as indicator reaction (see Analytical Biochem. 40,281 (1971)). Other substrates are described in the German Offenlegungsschrift 33 45 748 and the German Offenlegungsschrift 34 11 574.

Typical concentration ranges of the main reagents for the enzymatic determination at 37° C. of sodium ions using a 10 μl sample of plasma or serum are:

β-D-galactosidase 25 U/l to 7500 U/l
NPG 0.25 mmol/l to 5 mmol/l
Kryptofix ®221 0 mmol/l to 10 mmol/l
buffer, pH 7–9.5 200 mmol/l to 500 mmol/l
$Mg^{2+}$ 0.0 1 mmol/l to 10 mmol/l
EGTA (Lithium salt) 0 mmol/l to 20 mmol/l
Serum albumin 0 g/l to 5 g/l EGTA means Ethylenbis(oxyethylennitrilo)-tetraacetic acid. It will also be feasible to perform the analysis of sodium and potassium ions enzymatically in the same cuvette in the form of a twin test (see Example G).

Determination of Calcium Ions

For the measurement of calcium ions, a sample of blood plasma (or other body fluid) is incubated with a buffered mixture containing the peptide substrate succinyl-leucine-methionine-p-nitroanilide and the enzyme Calpain I. The reaction catalyzed by Calpain I is dependent on the presence of calcium ions and the rate of activity is a measure of the calcium ion concentration. A key feature of the method is the use of chelators capable of specifically binding calcium ions in order to lower their concentration to a range over which the enzyme is most sensitive. Under the conditions chosen for analysis, which include the presence of L-cysteine and 2-mercaptoethanol, the rate of p-nitroaniline formation is virtually proportional to the concentration of calcium being measured.

Preferred peptide substrates can be described by the general formula

$$R\text{-}P_n\text{-}P_2\text{-}P_1\text{-}X$$

whereby R represents acetyl, benzoyl, carbobenzoxy, succinyl, tert-butoxy carbonyl or 3-(2-furyl)acryloyl; $P_n\text{-}P_2\text{-}P_1$ represents a peptide chain of at least 2 residues with a preference for Tyr, Met, Lys or Arg in the $P_1$ position and a Leu or Val residue in the $P_2$ position; and X represents a chromogenic or fluorogenic group which is liberated by the action of the enzyme to yield a detectable change in colour or fluorescence. X can be a nitrophenyl, naphthyl or thiobenzyl ester as well as a nitroaniline, naphthylamine or methylcoumarin group either with or without further substituents on the aromatic ring. Some suitable peptide derivatives have also been described by T. Sasaki et al. in J. Biol. Chem. 259, 12489–12494, examples are succinyl-Leu-Met-MCA (MCA=4-methylcoumarin-7-amide), succinyl-Leu-Tyr-MCA, succinyl-Leu-Leu-Val-Tyr-MCA and tert-butoxy carbonyl-Val-Leu-Lys-MCA. Further synthetic substrates are described in Bergmeyer HU (Ed) Methods of Enzymatic Analysis, 3rd Edition, Volume 5, p. 84–85 (1984).

The concentration ranges of the compounds for such a determination method and reagents are:
Calpain I 1 000 U/l to 40 000 U/l*
Suc-Leu-Met-p-nitroanilide 1 mmol/l to 20 mmol/l
Chelator 0.01 mmol/l to 1 mmol/l
L-Cysteine 1 mmol/l to 10 mmol/l
2 - Mercaptoethano 1 1 mmol/l to 10 mmol/l
Buffer Imidazole-HCl 1 10 mmol/l to 100 mmol/l
pH 6–8 (preferred range 7–7.5)

The astrisk * means that unit is defined as the quantity of enzyme which increases the absorbance at 750 nm by 1.0 after 30 min of incubation at 30° C. with casein as substrate (N. Yoshimura et al., J. Biol. Chem. 258, 8883–8889, (1983)).

Any buffer having a pK in the required pH range with a negligible binding capacity for calcium may be used in the assay. Many of the Good-type buffers (N. E. Good et al., Biochem. 5, 467–477 (1966)) such as Tris, HEPES, MOPSO, BES, TES and imidazole fulfill these requirements (see example H). Collagenase may be used instead of Calpain I, and assayed fluorometrically at pH 6.5–7.5 with L-isoleucyl-L-analylglycyl ethylester, 0.02 mmol/l to 0.2 mmol/l.

Determination of Chloride Ions

For the determination of chloride in blood, plasma is incubated with a buffered mixture containing 0.01 mol/l cysteamine, 4 mmol/l Gly-Phe-p-nitroanilide and 0.2 U/ml Cathepsin C. The formation of p-nitroaniline is entirely dependent on the presence of the chloride anions. Selective binding agents may be added in addition in order to eliminate interference by bromide ions or to decrease the activity of chloride ions so as to adjust their concentration to the optimal range of the enzyme. Under the conditions chosen for analysis (see example 5) the rate of formation of p-nitroaniline:

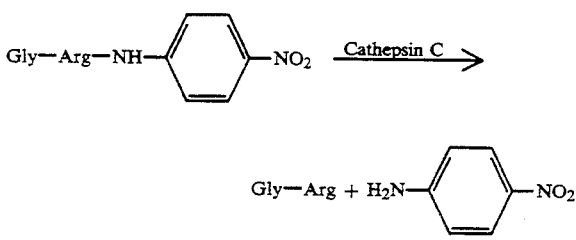

is proportional to the concentration of chloride ions in the sample. In this example the rate of the reaction is determined by measurement of the increase of absorption at 405 nm.

The concentration ranges of the compounds of such a determination method are:

citrate buffer 0.0 1–0.2 mol/l
pH 4–7 (preferred: 5.0–5.5)
cysteamine 1–20 mmol/l
gly-arg-p-nitroanilide 1–20 mmol/l
cathepsin C 2–100 mU/ml Any buffer having a pK in the required pH-range and a negligible chloride concentration may be used in the assay. Examples of enzymes from all of the categories listed above (transferases, hydrolases, oxidoreductases and lyases) have been shown in the literature to have a chloride dependency, especially if the origin of these enzymes is from halophilic organisms. The chloride dependency of Enzymes of the peptidase type has been extensively described. For examples dipeptidylpeptidase I (Cathepsin C), EC 3.4.14.1 (J. Ken Mc Donald, Bloch. Bioph. Res. Communication, 24 (5) 1966, 771f) or dipeptidylpeptidase III EC. 3.4.14.3 (J. Ken Mc Donald, Journal of Biol. Chem. 241 (7) 1966, 1494f), both catalyzing the hydrolysis of oligopeptide derivatives from the amino terminal end. Another example is the angiotensin converting enzyme EC 3.4.15.1 which is a dipeptidylcarboxypeptidase that catalyses the hydrolytic release of dipeptides from the carboxyl terminus of a broad range of oligopeptides (P. Bunning et al., Bioch. 26, 1987, 3374f; R. Shapiro et al., Bioch. 22, 1983, 3850f).

Instead of Gly-Arg-p-nitroanilide different other dipeptide- or oligopeptide substrates may be used. Preferred peptide substrates can be described by the general formula $R-P_n-P_1-X$ whereby for the dipeptidyl peptidase enzymes R=H and $Pn_n-P_1$ represents a peptide chain of at least 2 residues. X represents a chromogenic or fluorogenic group which is liberated by the action of the enzyme to yield a detectable change in colour or fluorescence. X can be a nitrophenyl-, naphthyl- or thiobenzylester as well as a nitroaniline, naphthylamine or methylcoumarin group either with or without further substituents on the aromatic ring. In the case of dipetidylcarboxypeptidase enzymes X represents the amino terminal and of the peptide chain an R is a chromogenic or fluorogenic group which is liberated by the action of the genzyme. R can be a N-2-furanacryloyl- or benzoyl-group either with or without further substituents (see example I).

As a further example of the enzymatic determination of chloride ion (Example J), plasma is incubated with a buffered mixture containing 4,6-ethylidene($G_7$)-p-nitrophenyl($G_1$)- ,D-maltoheptaoside (4,6-ethylidene-$G_7$PNP) (5 mmol/l), α-amylase (0.60 U/ml) and α-glucosidase (=30 U/ml). The formation of p-nitrophenol is entirely dependent on the presence of chloride anions, once again using either predilution, small sample volumenes or selective binding agents to adjust chloride ion concentration to the optimal range of the enzyme. The test principle is summarised below, and the rate of the reaction is determined by the measurement of the increase in absorption at 405 nm.

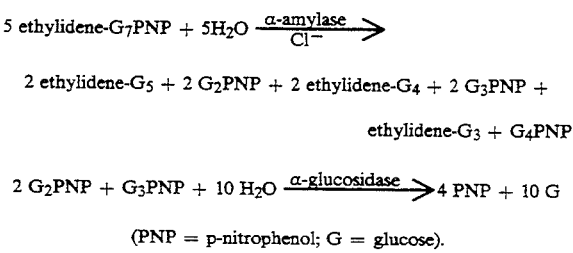

(PNP = p-nitrophenol; G = glucose).

The concentration ranges of compounds used for such a determination are:

Hepes or alternative chloride free buffer 0.01–0.5 mmol/l
pH 6.5–7.5
α-amylase 60–6000 U/l
α-glucosidase 3000–300 000 U/l 4,6- ethylidene-$G_7$PNP 0.5–10 mmol/l Assay variations discussed above for Cathepsin C (Example I) also apply to Example J.

Determination of Heavy Metal Ions

These metals bind tightly to cryptands such as Kryptofix ®221 and Kryptofix ®222. They will therefore displace other metals that are more loosely bound. An example of a metal ion readily displaced is zinc. Zinc ions are present in very low concentration in plasma. Thus it is feasible to add zinc ions complexed to K 221 to a buffered serum mixture. If a heavy metal is present the zinc ions will be liberated and their presence can be detected by stimulation of pyridoxal kinase (from sheep brain) an enzyme which is highly sensitive to zinc ions. Many other similar competitive binding assays are feasible, and those described are given by way of example and not of limitation.

Determination of Bicarbonate Ions

Bicarbonate ions can be measured using a variation of the principles embodied in the invention. Many ligands, e.g. the cryptands, are pH sensitive, and this property can be exploited to measure bicarbonate. Essentially, advantage is taken of the ability of bicarbonate to neutralize protons. It can be shown that the pH of a very lightly buffered serum sample, to which hydrochloric acid has been added will vary as a function of the bicarbonate concentration. The final pH is detected by the amount of free sodium ions (as detected with $\beta$-galactosidase) present in the presence of a pH-sensitive ion-binding agent such as Kryptofix®221, and this is a function of the original bicarbonate concentration. In essence, serum is acidified to pH 4.5 approx, with an equal volume of HCl (75 mmol/l) to convert all bicarbonate to hydroxyl ions, and then reacted with an assay system at pH 7.5–7.8, using a dilute Tris buffer (5 mmol/l) which incorporates an ion-selective enzyme, such as $\beta$-galactosidase and appropriate pH-sensitive ion binding agent. The sodium ion concentration of the sample must be known to obtain accurate results since a correction is necessary based on the quantity of sodium ions in the sample. The method is substantially more sensitive than procedures using chromogenic indicators as pH detectors (Example K).

Typical concentration ranges of the main reagents for the enzymatic determination at 37° C. of bicarbonate ions using a 10 $\mu$l sample of plasma or serum are:
$\beta$-D-galactosidase 250 U/l to 7500 U/l
NPG 0.25 mmol/l to 5 mmol/l
Kryptofix®221 0.2 mmol/l to 5 mmol/l
buffer, pH 7.5–7.8 1 mmol/l to 10 mmol/l
$Mg^{2+}$ 0.01 mmol/l to 10 mmol/l
EGTA (L i salt) 0.1 mmol/l to 5 mmol/l
Serum albumin 0 g/l to 5 g/l The need to correct for sodium ion concentration can be avoided by using an enzyme (e.g. pyridoxal kinase) sensitive to trace metals (e.g. zinc ions) normally present in plasma in ulcromolar concentration. Provided that the binding of the trace metal to its binding agent is pH sensitive and possesses a similar affinity to sodium ions for Kryptofix®221, bicarbonate ions can be measured by including the zinc ions in the reaction mixture in concentrations sufficiently in excess of those that can be encountered in plasma. Hence endogenous zinc ions will not interfere.

The methods as described above are simple, very rapid, accurate and precise and can be performed with inexpensive apparatus. The laboratory hazard of inflammable gases can be avoided as can the many problems associated with ion-selective electrodes. The method can be adapted for use with large equipment performing multiple analyses, yet can also be employed with inexpensive stand-alone instruments for emergency use close to the bedside. The packaging of the method in kit form is straightforward. Moreover, the determination of potassium and sodium ion concentration can be performed sequentially in the same cuvette (Example G). It is also intended that the method be useful for Doctors' offices with a machine employing dry chemistries. Although these methods have been developed using automatic spectrometers, they are readily adaptable to automated or manual laboratory equiment such as fluorimeters, luminometers, isotope counters etc.

The present invention will now be described in more detail with reference to the following examples, on the basis of a serum or plasma sample of 10 $\mu$l. These examples are given by way of illustration and not of limitation.

In the following Examples a small volume of sample (10 $\mu$l except where otherwise indicated in the case of serum or plasma) is mixed with Reagent 1, containing buffered substrate and certain cofactors, and incubated for a period of time, generally 0.1–5 min. Absorbance readings are normally taken at regular intervals during this incubation period. Reagent 2, containing the indicator enzyme is then added and the reaction rate monitored. In some Examples, Reagent 1 contains the indicator enzyme and Reagent 2 the appropriate substrate. The Examples show the final reaction mixture after the sample, Reagent 1 and Reagent 2 have been mixed.

EXAMPLE A

Measurement of Potassium Ion Concentration Using Pyruvate Kinase without a Sodium-Ion-Binding Agent, Sodium Ion Concentration Unknown.

The final incubation mixture contains:

175 mmol/l Tris-HCl buffer, pH 7.4
20 mmol/l $Li^+$ [17 mmol/l LiOH, 3 mmol/l LiCl]
3.0 mmol/l $MnCl_2$
2.6 mmol/l ADP (free acid)
2.9 mmol/l PEP (neutralized tris salt)
0.4 mmol/l NADH
17000 U/l LDH (assayed at 25° C.)
890 U/l PK from Bacillus stearothermophilus
4.0 mmol/l KG
8600 U/l GDH (in glycerol; assayed at 25° C.)
140 mg/l Human serum albumin Potassium ion standards (calibrating solutions) contain 140 mmol/l sodium ions to compensate for the stimulatory effect of sodium ions, present in plasma, on pyruvate kinase.

EXAMPLE B

Measurement of Potassium Ion Concentration Using Pyruvate Kinase, without a Sodium Ion Binding Agent, Sodium Ion Concentration Known.

The incubation mixture and calibrating solution are the same as for Example A.

A correction may be made for the sodium ion concentration of the mixture by adding (or subtracting) 0.1 mmol/l potassium for every 10 mmol/l the sodium ion concentration is below (or above) 140 mmol/l sodium ions. However, this correction should be verified by analysing aqueous solutions containing known sodium and potassium concentrations.

EXAMPLE C

Measurement of Potassium Ion Concentration Using Pyruvate Kinase in the Presence of a Sodium Ion-Binding Agent.

As for Example B, but human serum albumin is omitted and the medium contains in addition 6 $\mu$mol of Kryptofix®221 per assay. A pH of 7.8 is selected to minimise variations in displacement of sodium ions from Kryptofix®221 due to the differing potassium ion content of individual specimens.

EXAMPLE D

Measurement of Sodium Ion Concentration Using $\beta$-D-galactosidase

Variation a: The final incubation mixture contains:

300 mmol/l Tris HCl, pH 8.7 (37° C.)
4 mmol/l Dithiothreitol
7.5 mmol/l Magnesium sulphate
16 mmol/l Lithium chloride
0.44 mmol/l EGTA (lithium salt)
460 mg/l Human Serum Albumin
760 β-Galactosidase
1.5 mmol/l NPG
1.25 μmol/assay Kryptofix ®221

The reaction is monitored at 420 nm (or nearby) wavelength to determine the rate of formation of free 2-nitrophenol and hence the concentration of sodium ions in the original sample.

Variation b: An alternative approach compared with Variation a would be to reduce the sample concentration ten-fold by pre-dilution or to use a small sample volume, in which case the cryptand could be omitted.

Variation c: Measurement in fluids of low sodium ion content (e.g. <20 mmol/l) in which case the cryptand could be omitted.

EXAMPLE E

Measurement of Sodium Ions with Pyruvate Kinase (Direct Stimulation of Enzyme Activity by Sodium Ions, Under Conditions where Sensitivity of Potassium ions is Diminished).

Variation a: Incubation mixture contains for a 10 μl plasma sample:

300 mmol/l Tris HCl, pH 8.7 (37° C.)
5 mmol/l MgCl$_2$
2.6 mmol/l ADP (free acid)
2.9 mmol/l PEP (neutralized Tris salt)
0.34 mmol/l NADH
17 000 U/l LDH (assayed at 25° C.)
2 000 U/l PK (from rabbit muscle, assayed at 37° C.)
4 mmol/l KG
8 600 U/l GDH in glycerol (assayed at 25° C.)
1.25 μmol/assay Kryptofix ®222

Sodium ion calibrating solutions contain 4 mmol/l potassium to compensate for the potassium activating effect of serum potassium ions on pyruvate kinase.

EXAMPLE F

Measurement of Sodium Ions with Pyruvate Kinase (Competitive Binding Assay)—Potassium Ion Concentration Known The final incubation mixture contains for a 10 μl plasma sample:

300 mmol/l Glycine, pH 9.8
5 mmol/l MgCl$_2$
2.6 mmol/l ADP (free acid)
2.9 mmol/l PEP (neutralized tris salt)
0.34 mmol/l NADH
17 000 U/l LDH (assayed at 25° C.)
890 U/l PK from Rabbit muscle (assayed at 37° C.)
4 mmol/l KG
8 500 U/l GDH (assayed at 25° C.)
5 mmol/l KCl
2.5 μmol/assay Kryptofix ®221

Potassium chloride is added to this reagent and displaced stoichiometrically from Kryptofix ®221 by sodium ions, thus allowing the sodium ion concentration of the specimen to be quantified.

EXAMPLE G

Measurement of Potassium and Sodium Ion Concentration in the Same Cuvette (Twin-Test)

Sodium ion concentration is assayed first as in Example D except that the assay also contains:

2.6 mmol/l ADP (free acid)
2.9 mmol/l PEP (neutralized Tris salt)
0.4 mmol/l NADH
4.0 mmol/l KG
8 600 U/l GDH Following the measurement of sodium ions by means of determination fo the reaction rate, the pH of the incubation mixture is lowered to pH 7.4 with a hydrochloric acid aliquot.

Then the following ingredients are added to achieve the final concentrations indicated:

17 000 U/l LDH
890 U/l PK from Bacillus stearothermophilus
3.0 mmol/l MnCl$_2$
20.0 mmol/l LiCl The reaction rate may then be monitored at 340 nm but may also be measured at a slightly higher wavelength to minimise possible interference by the 2-nitrophenol liberated in the sodium ion indicator reaction.

EXAMPLE H

Measurement of Calcium Ion Concentration Using Calpain I

In this embodiment, a small sample of blood is centrifuged to obtain plasma. For the measurement of calcium ions the sample was incubated with a mixture containing 50 mmol/l imidazole-HCl buffer, pH 7.3, 5 mmol/l L-cysteine, 2.5 mmol/1 2-mercaptoethanol, 0.1 mmol/l EGTA and 5 mmol/l Suc-Leu-Met-p-nitroanilide at 30° C. The increase of absorbance at 405 nm was monitored over at 5 min interval. The rate is proportional to the calcium ion concentration of the sample.

EXAMPLE I

Measurement of Chloride Ion Concentration using Cathepsin C

In this embodiment a small sample of blood is centrifuged to obtain plasma (5 μl). For the measurement of chloride ion the incubation mixture contains 0.05 mol/l citrate buffer pH-5.0, 10mmol/l cysteamine and 4 mmol/l gly-arg-p-nitroanilide and 0.01 U/ml cathepsin C. The latter has been dialyzed against 10 mmol/l sodiumphosphate buffer (pH- 6.8)and 43% (v/v) of glycerol in order to remove chloride ions.

EXAMPLE J

Measurement of Chloride Ion Concentration Using -Amylase

Inhibition mixture contains for a 5 μl plasma sample:

Hepes or alternative chloride free buffer 100 mmol/l pH 7.1
α-Amylase 600 U/l
α-Glucosidase 30 000 U/l
4,6-Ethylidene-G$_7$PNP 5 mmol/l The reaction is monitored at 405 nm (or nearby wavelength to determine the rate of formation of free 4-nitrophenol and hence the concentration of chloride ions in the original sample.

EXAMPLE K

Measurement of Bicarbonate Ion Concentration using β-D-galactosidase

Variation a: The final incubation mixture contains:

5 mmol/l Tris HCl, pH 7.8 (37° C.)
4 mmol/l Dithiothreitol
7.5 mmol/l Magnesium sulphate
16 mmol/l Lithium chloride
0.44 mmol/l EGTA (lithium salt)
460 mg/l Human serum albumin
1500 U/l β-Galactosidase
1.5 mmol/l NPG
2.0 μmol/assay Kryptofix ®221

EGTA means Ethylenbis(oxyethylennitrilo)-tetraacetic acid. The sample is pre-incubated with an equivalent volume of HCl (for plasma, 75 mmol/l) to reduce sample pH to 4.5. The reaction is then monitored at 420 nm (or nearby) wavelength to determine the rate of formation of free 2-nitrophenol and hence to concentration of bicarbonate ions in the original sample. A correction is made for sodium ion concentration in the original specimen.

Variation b: Pyridoxal kinase, pyridoxal and zinc ions are substituted for β-galactosidase and NGP.

We claim:

1. Process for the determination of the concentration of an analyte ion in a fluid sample, comprising measuring the activity of an enzyme stimulated by an indicator ion, said enzyme selected from the group consisting of a transferase, a hydrolase, an oxidoreductase or a lyase in the presence of a selective binding agent and said indicator ion, wherein the selective binding agent forms a complex with the indicator ion and the indicator ion is displaced stoichiometrically from the complex by the analyte ion, whereby the displaced indicator ion stimulates the activity of the enzyme, wherein the activity of the enzyme is proportional to the concentration of analyte ion in the fluid sample.

2. Process according to claim 1, wherein said fluid sample is water.

3. Process according to claim 1, wherein said fluid sample is a body fluid.

4. Process according to claim 3, wherein said body fluid is blood, serum, plasma, urine, sweat, exudates or transudates.

5. Process according to claim 3, wherein the enzyme is a transferase transferring phosphorus-containing groups.

6. Process according to claim 5, wherein the transferase is selected from the group consisting of pyruvate kinase, hexokinase, adenylate kinase, pyridoxal kinase or acetate kinase.

7. Process according to claim 3, wherein the enzyme is selected from the group consisting of a hydrolase or a protease.

8. Process according to claim 7, wherein the hydrolase is selected from the group consisting of α- or β-D-galactosidase, carboxypeptidase A, collagenase, amylase, Calpain I, Calpain II, or dipeptidyl aminopeptidase I (Cathepsin C).

9. Process according to claim 8, wherein the hydrolase is α- or β-D-galactosidase or carboxypeptidase A.

10. Process according to claim 3, wherein the enzyme is an oxidoreductase.

11. Process according to claim 10, wherein the oxidoreductase is selected from the group consisting of glycerol dehydrogenase, acetaldehyde dehydrogenase or tyrosinase.

12. Process according to claim 3, wherein the enzyme is a lyase.

13. Process according to claim 12, wherein the lyase is a carbon-carbon lyase or a carbon-oxygen lyase.

14. Process according to claim 12, wherein the lyase is aldolase or carbonic anhydrase.

15. Process according to claim 3, wherein the analyte ion is selected from the group consisting of potassium, sodium, calcium, magnesium, manganese, lithium, lead, zinc, copper, iron, chloride, ammonium or substances that give rise to the formation of ammonium.

16. Process according to claim 3, wherein the analyte ion is potassium and the enzyme is selected from the group consisting of pyruvate kinase, glycerol dehydrogenase or acetaldehyde dehydrogenase.

17. Process according to claim 3, wherein the analyte ion is sodium and the enzyme is pyruvate kinase or β-D-galactosidase.

18. Process according to claim 3, wherein the selective binding agent is selected from the group consisting of a cryptand, coronand, podand, crown ether, spherand, hemispherand, calixaren, a natural occurring ionophore, a cyclic peptide, a complexone or a chelating agent, an alkali metal, or an alkaline earth metal.

19. Process according to claim 3, wherein the enzyme is pyruvate kinase, the indicator ion is potassium, the binding agent Kryptofix 221 and the analyte ion is sodium.

20. Process according to claim 3, wherein the enzyme is kinase, the indicator ion is $Mg^{2+}$, the binding agent is a chelating agent and the analyte ion is a metal.

21. Process according to claim 3, wherein the enzyme is pyridoxal kinase, the indicator ion is $Zn^{2+}$, the binding agent is Kryptofix 221 and the analyte ion is a heavy metal.

22. Process according to claim 3, wherein said selective binding agent is selected from the group consisting of a cryptand and a chelating agent.

23. A composition for the determination of the concentration of an analyte ion in a fluid sample, comprising an indicator ion, an enzyme stimulated by said indicator ion, said enzyme selected from the group consisting of a transferase, a hydrolase, an oxidoreductase or a lyase and a selective binding agent that forms a complex with the indicator ion whereby the indicator ion is displaced stoichiometrically from the complex by said analyte ion in said fluid sample wherein the activity of the enzyme is proportional to the concentration of analyte ion in the fluid sample.

* * * * *